(12) United States Patent
Charles

(10) Patent No.: US 7,824,089 B2
(45) Date of Patent: Nov. 2, 2010

(54) GRADIENT INDEX SURGICAL ILLUMINATOR

(75) Inventor: Steven T. Charles, Memphis, TN (US)

(73) Assignee: Alcon, Inc., Hunenberg (CH)

( * ) Notice: Subject to any disclaimer, the term of this patent is extended or adjusted under 35 U.S.C. 154(b) by 234 days.

(21) Appl. No.: 11/865,381

(22) Filed: Oct. 1, 2007

(65) Prior Publication Data

US 2008/0080206 A1    Apr. 3, 2008

Related U.S. Application Data

(60) Provisional application No. 60/848,972, filed on Oct. 3, 2006.

(51) Int. Cl.
    *A61B 1/06*     (2006.01)
(52) U.S. Cl. ...................................... 362/572; 362/573
(58) Field of Classification Search ......... 362/572–575, 362/577, 551, 804, 326, 339; 606/4, 17
See application file for complete search history.

(56) References Cited

U.S. PATENT DOCUMENTS

| 4,865,029 A | * | 9/1989 | Pankratov et al. ............... 606/4 |
| 4,887,190 A | * | 12/1989 | Sadamune et al. .......... 362/560 |
| 5,624,438 A | | 4/1997 | Turner |
| 5,738,676 A | * | 4/1998 | Hammer et al. ................ 606/4 |
| 2005/0078910 A1 | * | 4/2005 | Hickingbotham ............ 385/31 |

FOREIGN PATENT DOCUMENTS

| DE | 10249674 A1 | 5/2004 |
| EP | 1522290 A1 | 4/2005 |

* cited by examiner

*Primary Examiner*—Bao Q Truong
(74) *Attorney, Agent, or Firm*—Jonathan E. Prejean

(57) ABSTRACT

A gradient index wide-angle illuminator is disclosed, one embodiment comprising: a light source for providing a light beam; an optical cable, optically coupled to the light source for receiving and transmitting the light beam; a handpiece, operably coupled to the optical cable to receive the light beam; an optical fiber, operably coupled to the handpiece, wherein the optical fiber is optically coupled to the optical cable to receive and transmit the light beam; an optical element, optically coupled to a distal end of the optical fiber, for receiving the light beam and transmitting the light beam to illuminate a surgical field, wherein the optical element comprises a gradient index lens; and a cannula, operably coupled to the handpiece, for housing and directing the optical fiber and the optical element. The optical element can be a small-gauge, divergent gradient index lens having a distal surface co-incident with the distal end of the cannula. For example, the optical element can be a 19, 20 or 25 gauge optical element. Further, the cannula and the handpiece can be fabricated from biocompatible materials.

18 Claims, 3 Drawing Sheets

GRADIENT INDEX SURGICAL ILLUMINATOR

CROSS-REFERENCE TO RELATED APPLICATIONS

This application claims priority under 35 U.S.C. §119 to U.S. Provisional Patent Application No. 60/848,972, filed Oct. 3, 2006, the entire contents of which are incorporated herein by reference.

TECHNICAL FIELD OF THE INVENTION

The present invention relates generally to surgical instrumentation. In particular, the present invention relates to surgical instruments for illuminating an area during eye surgery. Even more particularly, the present invention relates to a gradient index of refraction wide-angle illuminator for illumination of a surgical field.

BACKGROUND OF THE INVENTION

In ophthalmic surgery, and in particular in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle illuminators can thus illuminate a larger portion of the retina as required by current wide-angle surgical microscope systems and/or surgeon requirements. Currently existing wide-angle illuminators, however, display several disadvantages.

One disadvantage of prior art wide-angle illuminators for ophthalmic surgery is the high precision required in the fabrication of the surfaces of the lenses used in the distal end of the illuminators. These lenses (optical elements) are typically optically coupled to, for example, an optical fiber carrying light from an illumination source, and act to scatter or otherwise diverge the incoming light to illuminate a surgical field. The high precision required to produce these conventional optical elements makes miniaturization (required for surgical endoilluminators) more difficult and raises the cost of production.

Another disadvantage of currently available wide-angle illuminators is glare. Glare results when the source of the illumination is small and bright, and the user (e.g., an ophthalmic surgeon) has a direct line of sight to the small bright illumination source. Glare is unwanted stray radiation that provides no useful illumination, and either distracts an observer or obscures an object under observation. Current wide-angle illuminators typically use non-flat lenses that extend beyond the distal end of the cannula to deliver light to a surgical site. These non-flat, extending optical elements are used to provide increased (wide-angle) light dispersion, but have the disadvantage of being a bright point source of glare for the surgeon. Glare can be corrected for in current wide-angle illuminators, but typically only by reducing the total illumination light flux, which reduces the amount of light available for observation by the surgeon. For example, the "bullet probe" manufactured by Alcon Laboratories, Inc., of Fort Worth, Tex., achieves wide-angle illumination by using a bullet-shaped fiber having a surface diffusive finish to scatter light emanating from the distal end of an optical fiber. To reduce glare, the bullet probe can use a geometric shield, which reduces the illumination angle by reducing the overall available light flux.

A further disadvantage of some prior art wide-angle illuminators is that the rounded or pointed surface of their distal end optical elements provide a larger and more adherent surface for blood while in a surgical environment. Blood covering the optical element at the illuminator tip can result in thermal damage to the optical element and to the optical fiber carrying light from a high intensity light source due to increased heating of the optical element caused by the blood blocking light transmission.

Therefore, a need exists for a surgical wide-angle illuminator that can reduce or eliminate these and other problems associated with prior art wide-angle illuminators.

BRIEF SUMMARY OF THE INVENTION

The embodiments of the gradient index wide-angle surgical illuminator of the present invention substantially meet these needs and others. One embodiment of this invention is a small-gauge, gradient index wide-angle illumination surgical system comprising: a light source for providing a light beam; an optical cable, optically coupled to the light source for receiving and transmitting the light beam; a handpiece, operably coupled to the optical cable to receive the light beam; an optical fiber, operably coupled to the handpiece, wherein the optical fiber is optically coupled to the optical cable to receive and transmit the light beam; an optical element, optically coupled to a distal end of the optical fiber, for receiving the light beam and providing the light beam to illuminate a surgical field, wherein the optical element comprises a gradient index lens; and a cannula, operably coupled to the handpiece, for housing and directing the optical fiber and the optical element.

The optical element can be a small-gauge, gradient index lens having a radially gradient index of refraction and a distal surface co-incident with the distal end of the cannula. For example, the optical element can be sized for housing within a 19, 20 or 25 gauge cannula (e.g., about 0.75 mm to about 0.4 mm diameter optical element). Further, the cannula, optical element and the handpiece can be fabricated from biocompatible materials. The optical cable can comprise a first optical connector operably coupled to the light source and a second optical connector operably coupled to the handpiece (to optically couple the optical cable to the optical fiber housed within the handpiece and cannula). These connectors can be SMA optical fiber connectors. The optical element, optical fiber and optical cable (i.e., the optical fiber(s) within the optical cable) are of compatible gauge so as to transmit the light beam from the light source to the surgical field. For example, all three elements could be of equal gauge.

In some embodiments of this invention, the optical fiber can be operably coupled to the handpiece to enable linear displacement of the optical fiber (and hence the optical element) within the cannula. The handpiece can include a means, such as a push/pull mechanism, for adjusting the linear displacement of the optical fiber. Other adjusting means as known to those in the art can also be used. Adjusting the linear displacement of the optical fiber will change the amount by which the optical element extends past the distal end of the cannula. By adjusting the linear displacement of the optical fiber, the angle of illumination and the amount of illumination provided by the optical element from the light source to illuminate the surgical field (e.g., the retina of an eye) can be adjusted by the surgeon.

Other embodiments of the present invention can include a method for wide-angle illumination of a surgical field using a gradient index wide-angle illuminator in accordance with the teachings of this invention, and a surgical handpiece embodiment of the gradient index wide-angle illuminator of the present invention for use in ophthalmic surgery. Embodiments of this invention can be implemented as a handpiece connected to a cannula, or other housing, including a fiber optic cable terminating in a diffusive optical element. Further, embodiments of this invention can be incorporated within a surgical machine or system for use in ophthalmic or other surgery. Other uses for a gradient index wide-angle illuminator designed in accordance with the teachings of this invention will be known to those having skill in the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein.

DETAILED DESCRIPTION OF THE INVENTION

Preferred embodiments of the present invention are illustrated in the FIGURES, like numerals being used to refer to like and corresponding parts of the various drawings.

The various embodiments of the present invention provide for a small gauge (e.g., 19, 20, or 25 gauge) optical fiber based endo-illuminator device for use in surgical procedures, such as in vitreo-retinal/posterior segment surgery. Embodiments of this invention can comprise a handpiece, such as the Alcon-Grieshaber Revolution-DSP™ handpiece sold by Alcon Laboratories, Inc., Fort Worth, Tex., connected to a small gauge cannula (e.g., 19, 20, or 25 gauge). The inner dimension of the cannula can be used to house one, or a plurality of, optical fibers terminating at a gradient index optical element in accordance with the teachings of this invention. Embodiments of the wide-angle illuminator can be configured for use in the general field of ophthalmic surgery. However, it is contemplated and it will be realized by those skilled in the art that the scope of the present invention is not limited to ophthalmology, but may be applied generally to other areas of surgery where wide-angle illumination may be desired.

An embodiment of the variable-intensity, wide-angle illuminator of this invention can comprise a gradient index ("GRIN") optical element, which can have a radially gradient index of refraction, and a stem and a handpiece fabricated from biocompatible polymeric materials, such that the invasive portion of the wide-angle illuminator can be a disposable surgical item. Other embodiments of this invention also can comprise a GRIN optical element, as will be known to those having skill in the art. The GRIN optical element can be a diverging GRIN lens having plane optical surfaces. The optical element can also be a converging GRIN lens having a length chosen so that the lens image plane lies directly on the surface plane of the lens. Further, the optical element can have a surface diffusive finish on a distal surface to scatter light emanating from the distal end of an optical fiber coupled to the proximal surface of the optical element. Embodiments of this invention fabricated from biocompatible polymeric materials can be integrated into a low cost, articulated handpiece mechanism, such that these embodiments can comprise an inexpensive disposable illuminator instrument.

GRIN lenses can be used to focus and collimate light within a variety of fiber optic components. GRIN lenses focus light through a precisely controlled radial variation of the lens material's index of refraction from the optical axis to the edge of the lens. This allows a GRIN lens with flat or angle polished surfaces to collimate light emitted from an optical fiber or to focus an incident beam into an optical fiber. Lens end faces can have an anti-reflection coating to avoid unwanted back reflection.

Figure 1:
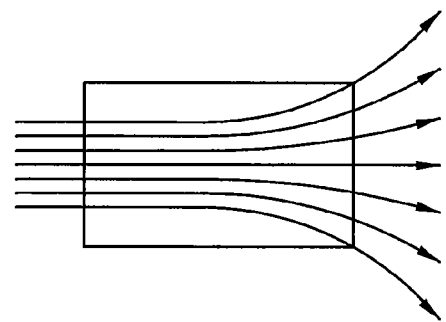
FIG. 1 is a diagrammatic representation of the light ray paths through a diverging GRIN lens.

GRIN lenses offer an alternative to the often-painstaking process of polishing curvatures onto glass lenses. By gradually varying the index of refraction within the lens material, light rays can be smoothly and continually redirected towards a point of focus. Alternatively, light rays can be diverged in a diverging GRIN lens having a parabolic-shaped refractive index profile with the minimum of the index at the center of the profile (lens centerline), as shown in FIG. 1. The internal structure of this index "gradient" can dramatically reduce the need for tightly controlled surface curvatures and results in simple and compact lens geometry. GRIN lenses can thus behave optically like conventional lenses, but do not need to be shaped like conventional lenses (instead of complicated shaped surfaces, plane optical surfaces can be used), simplifying the mounting of the GRIN lens and providing for good quality joints (bonds) between the lens and, for example, an optical fiber.

Figure 2:
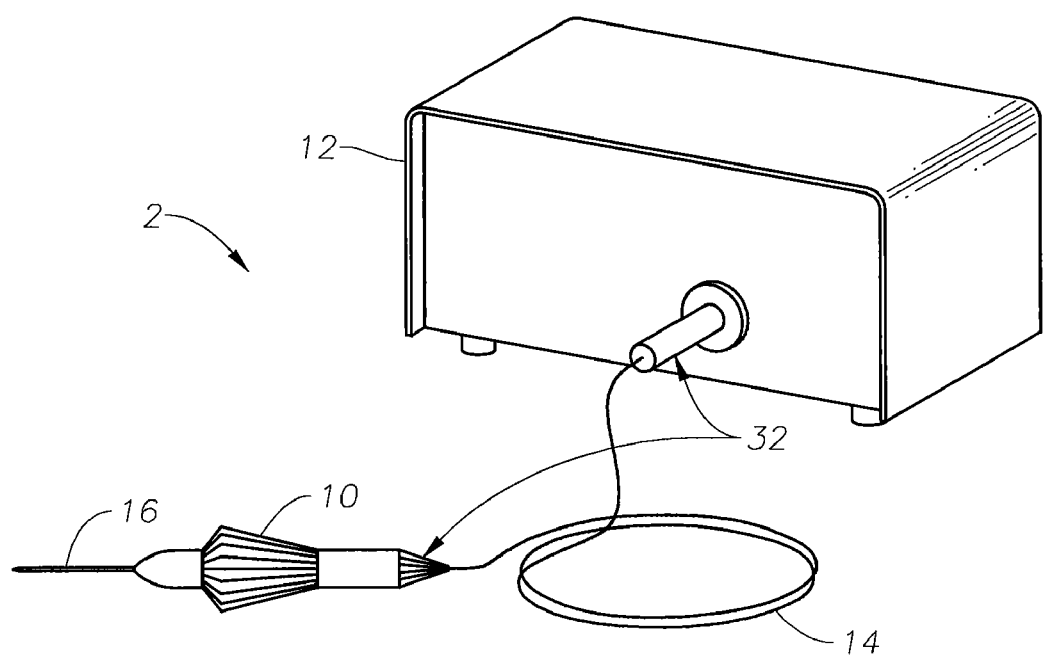
FIG. 2 is a diagrammatic representation of one embodiment of a system for gradient index wide-angle illumination in accordance with the teachings of this invention.

FIG. 2 is a diagrammatic representation of a surgical system 2 comprising a handpiece 10 for delivering a beam of relatively incoherent light from a light source 12 through cable 14 to a stem 16. Cable 14 can be any gauge fiber optic cable as known in the art, but is preferably a cable having 19, 20, or 25 gauge fiber. Further, cable 14 can comprise a single optical fiber or a plurality of optical fibers optically coupled to receive and transmit light from light source 12 to stem 16 through handpiece 10. Stem 16 is configured to house an optical element 20 at the distal end of stem 16, as is more clearly illustrated in FIG. 3. Coupling system 32 can comprise an optical fiber connector at each end of cable 14 to optically couple light source 12 to an optical fiber within handpiece 10, as discussed more fully below.

Figure 3:
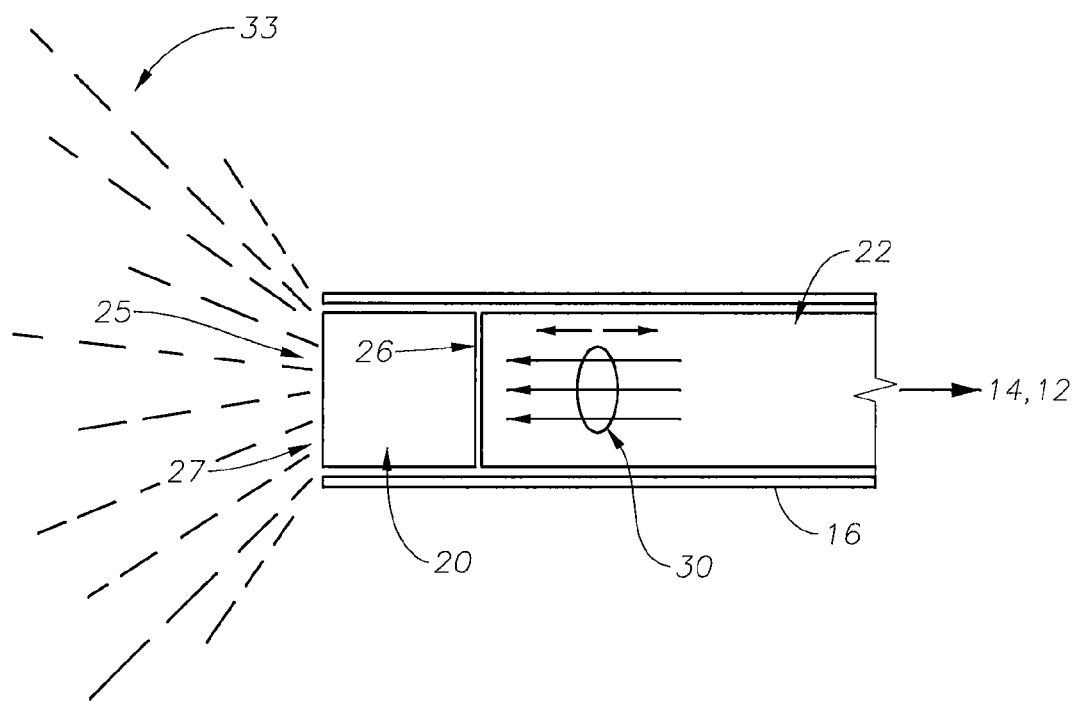
FIG. 3 is a more detailed diagram of a stem housing an embodiment of a gradient index optical element for wide-angle illumination in accordance with the teachings of this invention.

FIG. 3 is a magnified view of the distal end of stem 16 from FIG. 2. Stem 16 is shown housing fiber 22 and optical element 20. Optical element 20 is optically coupled to fiber 22, which can be optically coupled to fiber optic cable 14. In some embodiments, fiber optic cable 14 can instead extend through the handpiece 10 and can be optically coupled directly to optical element 20. For these embodiments, fiber 22 is not used. When implemented within handpiece 10, fiber 22 is of a gauge compatible with the gauge of fiber optic cable 14, such that it can receive and transmit light from fiber optic cable 14. Handpiece 10 can be any suitable surgical handpiece as known to those having skill in the art, such as the Revolution-DSP™ handpiece sold by Alcon Laboratories, Inc. of Fort Worth, Tex. Light source 12 can be a xenon light source, a halogen light source, or any other light source capable of delivering relatively incoherent light to fiber optic cable 14. Stem 16 can be a small gauge cannula, preferably on the order of 19, 20, or 25 gauge, and can be stainless steel or a suitable biocompatible polymer (e.g., PEEK, polyimide, etc.), as known to those having skill in the art.

Figure 5:
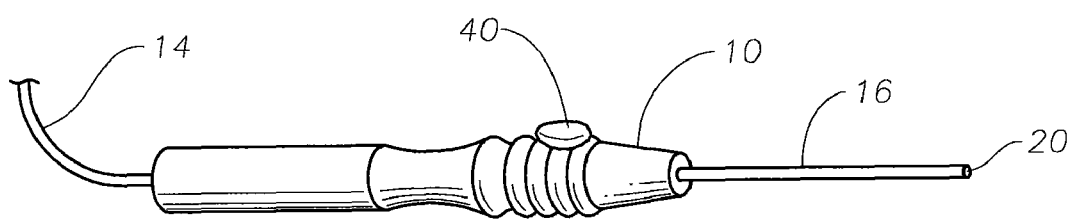
FIG. 5 is a diagram illustrating an embodiment of an adjusting means 40 in accordance with the present invention.

The fiber optic cable 14 (or fiber 22) housed within the stem 16 can be operably coupled to the handpiece 10, for example, via an adjusting means 40, as shown in FIG. 5. Adjusting means 40 can comprise, for example, a simple push/pull mechanism as known to those having skill in the art. Light source 12 can be operably coupled to handpiece 10 (i.e., to optically couple light source 12 to optical cable 14/optical fiber 22 and then to optical element 20) using, for example, standard SMA (Scale Manufacturers Association) optical fiber connectors at the end(s) of fiber optic cable 14. This allows for the efficient coupling of light from the light source 12 to fiber optic cable 14, through handpiece 10, and finally emanating from optical element 20 at the distal end of the stem 16. Light source 12 may comprise filters, as known to those skilled in the art, to reduce the damaging thermal effects of absorbed infrared or other radiation originating at the light source. The light source 12 filter(s) can be used to selectively illuminate a surgical field with different colors of light, such as to excite a surgical dye.

Fiber 22 (and/or 14, depending on the embodiment) is terminated by optically coupling to optical element 20. Fiber 22/optical cable 14 and optical element 20 can be optically coupled through direct contact, such as via an optical grade adhesive, as will be known to those having skill in the art. As discussed above, optical element 20 can be a GRIN lens, such as a diverging grin lens, having a radially gradient index of refraction such as shown in FIG. 1. Further, optical element 20 can have, in some embodiments, a surface diffusive finish 27 on a distal surface 25 to scatter light emanating from the distal end of optical fiber 22/14 coupled to the proximal surface 26 of the optical element 20. Distal surface 25 can be co-incident with the distal end of stem 16. Proximal surface 26 is optically coupled to the distal end of fiber 22/14. Optical element 20 is sized for housing within stem 16 (e.g., a 19 to 30 gauge cannula). For example, optical element 20 can have a diameter of about 0.4 mm to about 0.75 mm.

As shown in FIG. 3, optical element 20 can comprise a flat GRIN lens (or combination of GRIN lenses). Optical element 20 can be a commercially available miniature GRIN lens as will be known to those having skill in the art. In the exemplary embodiment of FIG. 3, light rays 30 from fiber 22/14 enter optical element 20 and exit as a divergent wide-angle pattern of light 33 from the distal surface 25 of optical element 20. The light rays 30 entering GRIN optical element 20 are bent in a divergent pattern, as shown, and in a manner illustrated in FIG. 1. In some embodiments, optical element 20 can comprise a surface diffusive finish 27 (shown) on distal surface 25 to scatter light transmitted by optical element 20 from the distal end of optical fiber 22/14. Surface diffusive finish 27 can comprise a diffusive optical coating as will be known to those having skill in the art. The optical element 20 is housed inside stem 16 (e.g., a small-gauge cannula of about 19 to 30 gauge). Stem 16 is itself operably coupled to the handpiece 10, which can be either a re-usable or a disposable handpiece 10.

Figure 4:
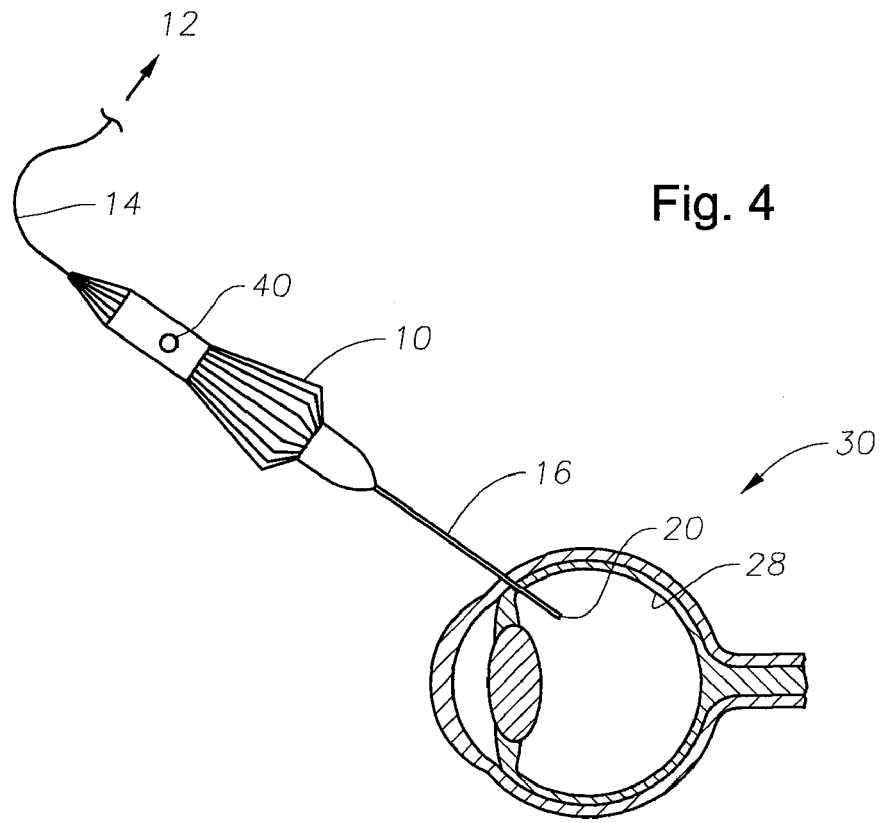
FIG. 4 is a diagram illustrating the use of an embodiment of a wide-angle illuminator of the present invention for ophthalmic surgery.

FIG. 4 illustrates the use of one embodiment of the gradient index wide-angle illuminator of this invention in an ophthalmic surgery. In operation, handpiece 10 delivers a beam of light through stem 16 (via optical fiber 22 and/or fiber optic cable 14) and through optical element 20 to illuminate a retina 28 of an eye 30. The collimated light delivered through handpiece 10 to optical element 20 is generated by light source 12 and can be delivered to illuminate the retina 28 by means of fiber optic cable 14 and coupling system 32. Optical element 20 spreads the light beam from light source 12 over as large an area of the retina as, for example, a microscopic wide-angle objective lens permits a surgeon to see.

FIG. 5 provides another view of a wide-angle illuminator according to the teachings of this invention showing more clearly an embodiment of adjusting means 40. In this embodiment, adjusting means 40 comprises a slide button, as known to those skilled in the art. Activation of adjusting means 40 on handpiece 10 by, for example, a gentle and reversible sliding action, can cause the fiber 22/14 (and hence the optical element 20) to move within stem 16 by an amount determined and adjusted by sliding adjusting means 40. Adjusting the linear displacement of the optical fiber 22 within stem 16 in this way can be used to change the distance that optical element 20 extends beyond the distal end of stem 16, and hence adjust the angle of dispersion/illumination of light exiting from optical element 20.

Thus, the angle of illumination and the amount of illumination provided by optical element 20 to illuminate the surgical field (e.g., the retina 28 of an eye 30) can be easily adjusted by a surgeon by adjusting the linear displacement of optical element 20/optical fiber 22. In this way, a surgeon can adjust the amount of light spread over a surgical field as desired to optimize the viewing field while minimizing glare. The adjusting means 40 of handpiece 10 can be any adjusting means known to those familiar with the art and can be coupled to optical fiber 22/14 by any means suitable to allow movement of optical fiber 22/14 as discussed herein. For example, adjusting means 40 can be, in a simple embodiment, coupled via an adhesive to optical fiber 22/14.

In one embodiment of the gradient index wide-angle illuminator of the present invention, a simple mechanical locking mechanism, as known to those skilled in the art, can permit the illumination angle (position of optical element 20) to be fixed, until released and/or re-adjusted by the user via the adjusting means 40. Thus, the pattern of light 33 emanating from the distal end of stem 16 will illuminate an area over a solid angle $\theta$, the angle $\theta$ being continuously adjustable by a user (e.g., a surgeon) via the adjusting means 40 of handpiece 10.

An advantage of the optical element 20 and of the embodiments of the gradient index wide-angle illuminator of this invention, is that an operator can continuously vary the intensity and angle of illumination of the pattern of light 33 exiting optical element 20 to optimize viewing conditions within the surgical field. The pattern of light 33 from optical element 20 can thus be focused and controlled as desired by the operator. The embodiments of the gradient index wide-angle illuminator of the present invention are therefore operable to adjust the angle and intensity of the light provided by light source 12 to substantially cover the area of the surgical field desired by a surgeon.

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide wide-angle and/or variable illumination.

What is claimed is:

1. A gradient index wide-angle illuminator, comprising:
   an optical fiber, optically coupled to a light source and operable to receive a light beam from the light source;
   a handpiece, operably coupled to the optical fiber;
   an optical element, optically coupled to a distal end of the optical fiber, for receiving the light beam and transmitting the light beam to illuminate a surgical field, wherein the optical element comprises a gradient index lens and wherein an index of refraction of the gradient index lens varies radially; and
   a cannula, operably coupled to the handpiece, for housing and directing the optical fiber and the optical element.

2. The gradient index wide-angle illuminator of claim 1, wherein the optical element is a small-gauge optical element having a distal surface co-incident with an open aperture of the cannula.

3. The gradient index wide-angle illuminator of claim 1, wherein the optical element is a 19, 20 or 25 gauge optical element.

4. The gradient index wide-angle illuminator of claim 1, wherein the optical fiber is optically coupled at the distal end to the optical element and at another end to an optical cable, wherein the optical cable is operably coupled to the light source to transmit the light beam to the optical fiber.

5. The gradient index wide-angle illuminator of claim 4, wherein a gauge of the optical cable and a gauge of the optical fiber are equal.

6. The gradient index wide-angle illuminator of claim 1, further comprising a surface diffusive finish on a distal surface of the optical element operable to scatter the light beam to illuminate the surgical field.

7. The gradient index wide-angle illuminator of claim 1, wherein the optical fiber is operably coupled to the handpiece to enable linear displacement of the optical fiber within the cannula.

8. The gradient index wide-angle illuminator of claim 1, wherein the light source is a xenon light source.

9. The gradient index wide-angle illuminator of claim 1, wherein the optical element is a diverging gradient index lens.

10. A gradient index wide-angle illumination surgical system comprising:
    a light source for providing a light beam;
    an optical cable, optically coupled to the light source for receiving and transmitting the light beam;
    a handpiece, operably coupled to the optical cable;
    an optical fiber, operably coupled to the handpiece, wherein the optical fiber is optically coupled to the optical cable to receive and transmit the light beam;
    an optical element, optically coupled to a distal end of the optical fiber, for receiving the light beam and transmitting the light beam to illuminate a surgical field, wherein the optical element comprises a gradient index lens and wherein an index of refraction of the gradient index lens varies radially; and
    a cannula, operably coupled to the handpiece, for housing and directing the optical fiber and the optical element.

11. The gradient index wide-angle illumination surgical system of claim 10, wherein the optical element is a small-gauge optical element having a distal surface co-incident with an open aperture of the cannula.

12. The gradient index wide-angle illumination surgical system of claim 10, wherein the optical element is a 19, 20 or 25 gauge optical element.

13. The gradient index wide-angle illumination surgical system of claim 10, wherein the optical fiber is part of the optical cable.

14. The gradient index wide-angle illumination surgical system of claim 10, wherein the optical fiber is operably coupled to the handpiece to enable linear displacement of the optical fiber within the cannula.

15. The gradient index wide-angle illumination surgical system of claim 10, wherein the light source is a xenon light source.

16. The gradient index wide-angle illumination surgical system of claim 10, wherein the optical element is a diverging gradient index lens.

17. The gradient index wide-angle illuminator of claim 1, wherein the index of refraction of the gradient index lens has a minimum value at a centerline of the gradient index lens parallel to the light beam received by the optical element.

18. The gradient index wide-angle illumination surgical system of claim 10, wherein the index of refraction of the gradient index lens has a minimum value at a centerline of the gradient index lens parallel to the light beam received by the optical element.

* * * * *